(12) United States Patent
Sarenac et al.

(10) Patent No.: US 11,564,562 B2
(45) Date of Patent: Jan. 31, 2023

(54) PREPARING A STRUCTURED OPTICAL BEAM FOR HUMAN OBSERVATION

(71) Applicant: Quantum Valley Investment Fund LP, Waterloo (CA)

(72) Inventors: Dusan Sarenac, Waterloo (CA); Connor Kapahi, Waterloo (CA); David G. Cory, Branchton (CA); Dmitry A. Pushin, Toronto (CA)

(73) Assignee: Quantum Valley Investment Fund LP

( * ) Notice: Subject to any disclaimer, the term of this patent is extended or adjusted under 35 U.S.C. 154(b) by 123 days.

(21) Appl. No.: 16/790,336

(22) Filed: Feb. 13, 2020

(65) Prior Publication Data
US 2020/0253469 A1   Aug. 13, 2020

Related U.S. Application Data

(60) Provisional application No. 62/804,883, filed on Feb. 13, 2019.

(51) Int. Cl.
*A61B 3/00* (2006.01)
*G02B 27/00* (2006.01)
(Continued)

(52) U.S. Cl.
CPC .......... *A61B 3/0008* (2013.01); *A61B 3/0075* (2013.01); *G02B 27/0081* (2013.01);
(Continued)

(58) Field of Classification Search
CPC ..... A61B 3/00; A61B 3/30008; A61B 3/0075; A61B 3/1225; G02B 27/00; G02B 27/28;
(Continued)

(56) References Cited

U.S. PATENT DOCUMENTS 8,400,713 B2   3/2013   Grasser
9,158,063 B2 * 10/2015   Curtis ................. G03B 21/208
(Continued)

FOREIGN PATENT DOCUMENTS

CN   103712781   4/2014
CN   108401447   8/2018
(Continued)

OTHER PUBLICATIONS

Wikipedia, "Confocal microscopy", Jan. 23, 2017 (Year: 2017).*
(Continued)

*Primary Examiner* — Jie Lei
(74) *Attorney, Agent, or Firm* — Henry Patent Law Firm PLLC (57) ABSTRACT

In a general aspect, a structured optical beam with position-dependent polarizations is prepared for human observation. In some examples, an optics method includes processing an optical beam to produce a structured optical beam for human observation. Processing the optical beam includes receiving the optical beam from a laser source; attenuating the optical beam to an exposure irradiance level that is safe for direct viewing by a human eye; expanding the optical beam to a size configured for a field of view of the human eye; and preparing the optical beam with a position-dependent polarization profile. The structured optical beam, which has the position-dependent polarization profile, is directed towards an observation region for human observation.

12 Claims, 3 Drawing Sheets

(51) Int. Cl.
G02B 27/48 (2006.01)
G02B 27/28 (2006.01)
G02F 1/21 (2006.01)
G02B 5/20 (2006.01)

(52) U.S. Cl.
CPC ........... *G02B 27/286* (2013.01); *G02B 27/48* (2013.01); *G02F 1/21* (2013.01); *G02B 5/205* (2013.01); *G02F 1/215* (2021.01)

(58) Field of Classification Search
CPC .. G02B 27/0081; G02B 27/286; G02B 27/48; G02B 27/1006; G02B 5/205; G02B 5/18; G02B 5/3083; G02B 21/0072; G02B 21/0068; G02F 1/21; G02F 1/215; G02F 2001/215
USPC ....... 351/213, 215, 221, 243, 205, 206, 208; 359/489.01, 489.06, 489.07, 189.16
See application file for complete search history.

(56) References Cited

U.S. PATENT DOCUMENTS

| | | | |
|---|---|---|---|
| 2003/0223064 A1* | 12/2003 | Anderson | A61B 3/14 356/364 |
| 2005/0069242 A1 | 3/2005 | Fujita et al. | |
| 2005/0195480 A1* | 9/2005 | Brown | G02B 21/0092 359/489.07 |
| 2006/0238865 A1 | 10/2006 | Biss et al. | |
| 2010/0231817 A1 | 9/2010 | Ide et al. | |
| 2010/0315597 A1 | 12/2010 | Powell et al. | |
| 2016/0154247 A1 | 6/2016 | Liu et al. | |
| 2019/0029510 A1 | 1/2019 | Temple | |

FOREIGN PATENT DOCUMENTS

| | | |
|---|---|---|
| JP | 2011145685 | 7/2011 |
| WO | 2018068038 | 4/2018 |

OTHER PUBLICATIONS

"Revision of Guidelines on Limits of Exposure to Laser Radiation of Wavelengths Between 400 nm and 1.4 μm", International Commission on Non-Ionizing Radiation Protection, Health Physics, vol. 79, No. 4, Oct. 2000, 10 pgs.
Sarenac , et al., "Direct discrimination of structured light by humans", arXiv:1910.04628v1, Oct. 10, 2019, 8 pgs.
"ICNIRP Guidelines on Limits of Exposure to Laser Radiation of Wavelengths Between 180 nm and 1,000 μm (revised)", Health Phys 105, 2013, 26 pgs.
Allen , et al., "Orbital angular momentum of light and the transformation of Laguerre-Gaussian laser modes", Phys. Rev. A 45, 8185, Jun. 1, 1992, 6 pgs.
Andersen , et al., "Quantized Rotation of Atoms from Photons with Orbital Angular Momentum", Physical Review Letters 97, 170406, Oct. 2006, 4 pgs.
Barnett , et al., "Optical orbital angular momentum", Philosophical Transactions of the Royal Society A 375, Jan. 2017, 9 pgs.
Beijersbergen , et al., "Helical-wavefront laser beams produced with a spiral phaseplate", Optics Communications, 112, Dec. 1, 1994, 7 pgs.
Bliokh , et al., "Semiclassical Dynamics of Electron wave Packet States with Phase Vortices", Phys.Rev.Lett. 99, Sep. 12, 2007, 6 pgs.
Bour , "Polarized Light and the Eye", Visual Optics and Instrumentation, 1999, 17 pgs.
Brullot , et al., "Resolving enantiomers using the optical angular momentum of twisted light", Science advances 2, e1501349, Mar. 2016, 6 pgs.
Clark , et al., "Controlling neutron orbital angular momentum", Nature 525, 504, 2015, 7 pgs.

Coren , "The use of Haidinger's brushes in the study of stabilized retinal images", Behavior Research Methods 7 Instrumentation 3, 1971, 4 pgs.
Field , et al., "Retinal Processing Near Absolute Threshold: From Behavior to Mechanism", Annu. Rev. Physiol. 67, Oct. 12, 2004, 27 pgs.
Forster , "The Clinical Use of the Haidinger's Brushes Phenomenon", American Journal of Ophthalmology 38, 1954, 1 pg.
Friese , et al., "Optical angular-momentum transfer to trapped absorbing particles", Physical Review A 54, 1593, Aug. 1996, 4 pgs.
Haidinger , "Ueber das directe erkennen des polarisirten lichts and der lage der polarisationsebene", Annalen der Physik 139, 1844, 12 pgs.
He , et al., "Direct Observation of Transfer of Angular Momentum to Absorptive Particles from a Laser Beam with a Phase Singularity", Physical Review Letters 75, 826, Jul. 31, 1995, 6 pgs.
Hecht , et al., "Energy, quanta, and vision", The Journal of General Physiology, Mar. 30, 1942, 22 pgs.
Hochheimer , et al., "Retinal Polarization Effects", Applied Optics, vol. 21, No. 21, Nov. 1, 1982, 8 pgs.
Holmes , et al., "Testing the Limits of Human Vision with Single Photons", Frontiers in Optics/Laser Science, 2015, 2 pgs.
Horvath , et al., "Celestial polarization patterns sufficient for viking navigation with the naked eye: detectability of haidinger's brushes on the sky versus meteorological conditions", Royal Society Open Science 4, Jan. 2017, 12 pgs.
Horvath , et al., "Polarized light in animal vision: polarization patterns in nature", Springer Science & Business Media, 2004, 2 pgs.
Knighton , et al., "Linear Birefringence of the Central Human Cornea", Investigative ophthalmology & visual science 43, Jan. 2002, 5 pgs.
Mair , et al., "Entanglement of the orbital angular momentum states of photons", Nature 412, 313, 2001, 4 pgs.
Maxwell , "Manuscript on experiments on the cause of haidingers brushes", The Scientific Letters and papers of James Clark Maxwell, Aug. 5, 1850, 4 pgs.
McMorran , et al., "Electron Vortex Beams with High Quanta of Orbital Angular Momentum", science 331, 192, 2011, 5 pgs.
Misson , "A Mueller matrix model of Haidinger's brushes", Ophthalmic and Physiological Optics 23, 2003, 7 pgs.
Misson , et al., "Computational simulation of Haidinger's brushes", Journal of the Optical Society of America (JOSA) A 35, May 11, 2018, 7 pgs.
Muller , et al., "Perception of Haidinger Brushes in Macular Disease Depends on Macular Pigment Density and Visual Acuity", Investigative Ophthalmology & Visual Science 57, Feb. 2016, 9 pgs.
Phan , et al., "Interaction of Fixed Number of Photons with Retinal Rod Cells", Phys.Rev.Lett. 112, 213601, May 2014, 5 pgs.
Rothmayer , et al., "Nonlinearity in the rotational dynamics of Haidinger's brushes", Applied optics 46, Oct. 5, 2007, 8 pgs.
Rubinsztein-Dunlop , et al., "Roadmap on Structured Light", J. Optics 19, 013001, 2016, 52 pgs.
Sarenac , et al., "Generation and detection of spin-orbit coupled neutron beams", PNAS, www.pnas.org/cgi/doi/10.1073/pnas. 1906861116, Aug. 30, 2019, 5 pgs.
Sarenac , et al., "Generation of a Lattice of Spin-Orbit Beams via Coherent Averaging", Physical Review Letters 121, 183602, Oct. 30, 2018, 6 pgs.
Sarenac , et al., "Holography with a neutron interferometer", Optics Express 24, 22528, Oct. 2016, 8 pgs.
Schwarz , et al., "Talbot Effect of orbital angular momentum lattices with single photons", arXiv:1908.01016, Aug. 2, 2019, 5 pgs.
Shurcliff , "Haidingers brushes and circularly polarized light", JOSA 45, 1955, 1 pg.
Simpson , et al., "Mechanical equivalence of spin and orbital angular momentum of light: an optical spanner", Optics Letters 22, Jan. 1, 1997, 3 pgs.
Stanworth , et al., "The Measurement and Clinical Significance of the Haidinger Effect", Transactions. Ophthalmological Society of the United Kingdom 75, 67, 1955, 13 pgs.
Tinsley , et al., "Direct detection of a single photon by humans", Nature Communications 7, 12172, Jul. 19, 2016, 9 pgs.

(56) References Cited

OTHER PUBLICATIONS

Uchida, et al., "Generation of electron beams carrying orbital angular momentum", nature 464, 737, Apr. 2010, 3 pgs.
Vannasdale, et al., "Determination of foveal location using scanning laser polarimetry", Journal of vision 9, 2009, 26 pgs.
Wang, et al., "Terabit free-space data transmission employing orbital angular momentum multiplexing", Nature Photonics 6, 488, 2012, 9 pgs.
Wickens, "Elementary Signal Detection Theory", Oxford University Press, US; pp. 26-29, 2002, 4 pgs.
WIPO, International Search Report and Written Opinion dated May 6, 2020, in PCT/CA2020/050188, 6 pgs.
EPO, Extended European Search Report dated Feb. 4, 2022, in EP 20755472.6, 11 pgs.
Cui, et al., "Speckle Suppression by Controlling the Coherence in Laser Based Projection Systems", Apr. 2015, 6 pgs.
Jiaqi, et al., "Eye-Safety Analysis of Infrared Laser Imaging for Security Surveillance", 2011 Int'l Conf. on Optical Instruments and Technology: Optoelectronic Imaging and Processing Technology, 2011, 9 pgs.

* cited by examiner

PREPARING A STRUCTURED OPTICAL BEAM FOR HUMAN OBSERVATION

CROSS-REFERENCE TO RELATED APPLICATIONS

This application claims priority to U.S. Provisional Application No. 62/804,883, filed Feb. 13, 2019 and entitled "Preparing Geometrical Phases and Quantum States for Human Observation," which is hereby incorporated by reference.

BACKGROUND

The following description relates to preparing a structured optical beam with geometrical phases and spatially dependent polarization profiles, for example, for observation by a human observer.

The fact that humans can perceive polarization state of light through an entoptic phenomenon was first described by Austrian physicist Wilhelm Karl von Haidinger in 1844. When viewing polarized light, a bowtie-like shape (now known as "Haidinger's brush") appears in the central point of the visual field. The perception of Haidinger's brushes depends on the presence of dichroic carotenoid pigments which are found in the macula, which is located at the center of the retina. The radially symmetric dichroic elements are centered on the foveola in the macula of the human eye and act as a radial polarization filter. This has led to studies that used Haidinger's brushes as a diagnosis of central visual field dysfunctions and age-related macular degeneration (AMD).

DETAILED DESCRIPTION

In some aspects of what is described here, a structured optical beam having spatially dependent properties (e.g., geometrical phases, position-dependent polarization directions, etc.) is prepared by an optical system. In some implementations, a structured, optical beam with well-defined spatially dependent properties can be directed into an observation region where it can be directly observed by a human eye (e.g., the retina). Accordingly, Haidinger's brushes may be perceived by the human in response to the structured optical beam. In some cases, such a system allows the human eye to map out spatially dependent Pancharatnam-Berry geometrical phases in the structured optical beam based on the orientations of the Haidinger's brushes. Spatially dependent Pancharatnam-Berry geometrical phases typically manifest as spatially dependent polarization in optical beams.

In some aspects, the system and techniques described here may provide conditions under which a human (or potentially other subjects) can observe and analyze a coherent optical beam with spatially dependent polarizations. For example, the orientation of the brushes, along with determining whether the brush rotates with the rotation of one's head while the eye focuses on a point, may be used to determine the polarization state of light. In some implementations, the system and techniques described here may allow diagnosing the ability of a person to perceive Haidinger's brushes. Advantages may be achieved by the use of a spectrum of brush orientations in the beam, by the use of a single wavelength, by the testing of an observer's ability to determine the spatially dependent brush orientation, or a combination of these and other techniques and device properties.

Macular health determines clarity and structure of the perceived features. Direct perception and discrimination of structured optical beams is possible through the observation of distinct entoptic profiles induced by the interaction between the polarization gradients in an optical beam and the radially symmetric dichroic elements that are centered on the foveola in the macula of the human eye. In some aspects of what is described here, the system and technique can be utilized for diagnosis of retinal diseases, e.g., central visual field dysfunctions, and age-related macular degenerations (AMD). In some implementations, structure and the functionality of the macula may be determined by obtaining feedback from the observer about the clarity and structure of the observed features. In some implementations, the system and technique described here may offer several advantages over existing technologies. For example, the system and technique described here is less complex and cost-effective relative to traditional systems and techniques. Accordingly, the system and technique described here may not require highly trained medical professionals for performing certain operations.

In some implementations, the system and technique described here may be used for directly observing and discriminating quantized spatial modes and non-separable optical states with the human eye. In some cases, a structured optical beam can be used to carry well defined quantized spatial modes, which can be observed by human eye. For example, the system may be used to test a person's ability to directly observe and quantify the orbital angular momentum (OAM) number of an optical spin-orbit state.

Figure 1:
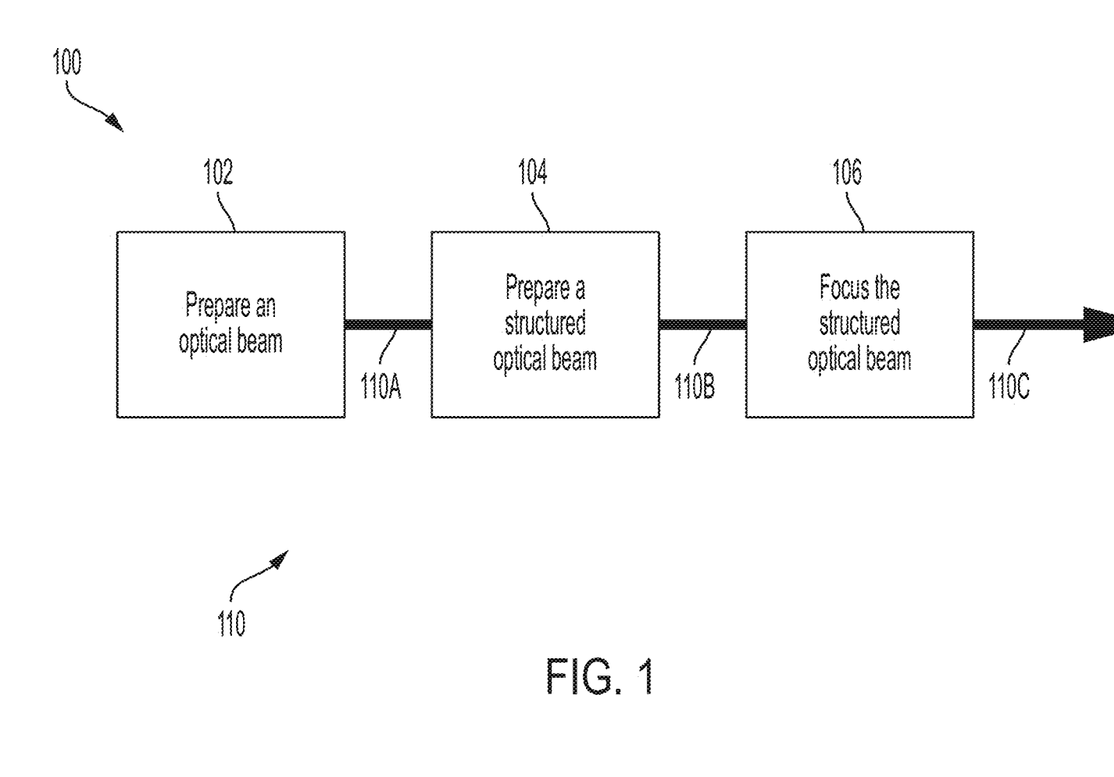
FIG. 1 is a flow chart showing aspects of an example process.

FIG. 1 is a flow diagram showing aspects of an example process 100. The example process 100 can be performed, for example, by one or more optical systems. For instance, operations in the example process 100 may be performed by the optical system 200 shown in FIG. 2 or another type of system with additional or different optical components. The example process 100 may include additional or different operations, including operations performed by additional or different components, and the operations may be performed in the order shown or in another order. In some cases, operations in the example process 100 can be combined, iterated or otherwise repeated or performed in another manner.

In some cases, the operations in the example process 100 shown in FIG. 1 are implemented as processes to construct a structured optical beam with position-dependent polarizations. In some cases, the process 100 may be implemented for testing the ability of a human eye in determining the spatially dependent orientation of Haidinger's brushes. In some instances, the structured optical beam with position-dependent polarizations may be used to encode quantized spatial modes for perception of human eyes.

At 102, an optical beam is prepared on a beam path 110. In some implementations, one or more optical elements are configured along the optical path 110. In some implementations, the optical beam is prepared by passing the optical beam through various optical components to obtain an expanded collimated optical beam on a first portion 110A of the beam path. In some implementations, an optical beam may be generated by a light source. For example, a coherent monochromatic light source, such as a laser source, may be used for creating a laser beam. In some instances, the optical beam may be generated by other types of light sources.

In some implementations, the optical beam from the light source may be blue light, for example, with a mean wavelength in a range of 450-470 nanometers (nm). For example, blue light may be preferred because the human perception of optical polarization has been found to be optimal at a wavelength of 460 nm. In some implementations, a diode laser for producing the optical beam with a central wavelength of 460 nm may be used as the light source. In some other examples, other types of light sources operating at a different wavelength or wavelength range may be used.

In some implementations, the optical beam from the light source may be attenuated to a pre-determined exposure irradiance level or below a threshold exposure irradiance level so that it is safe for direct viewing by a human eye without causing any damage to the human eye. In some implementations, one or more optical attenuators may be configured at the output of the light source. In some implementations, the attenuators may be configured to ensure that the exposure irradiance level of the optical beam for human observation is below the Maximal Permissible Exposure (MPE) value. For example, the MPE value for sustained exposure to light with wavelength ~460 nm is $10^{-4}$ W m$^{-2}$. In some implementations, optical attenuators based on power reduction principles such as absorption, reflection, diffusion, scattering, deflection, diffraction and dispersion may be used for attenuating the optical beam from the light source. In some implementations, the optical attenuator may include one or more fixed attenuators, one or more variable attenuators, or a combination of both. In some implementations, the attenuation coefficient of the optical attenuators may be controlled to adjust the exposure irradiance level according to the wavelength of the optical beam and/or the sensitivity of observer's eyes. In some examples, the attenuators are neutral-density filters. In other implementations, the attenuators may be configured at any point along the propagation direction of the optical beam. For example, a laser beam from a laser source may be attenuated to a level less than $10^{-3}$ W m$^{-2}$ at the observation region in order to comply with the guidelines outlined by the International Commission on Non-Ionizing Radiation.

In some implementations, the optical beam after the attenuators may be collimated and expanded. In some implementations, the optical beam is collimated and expanded to a size that covers at least 3-5 degrees of the field of view of the human eye. In some implementations, the collimating and broadening of the optical beam is achieved by passing the optical beam through one or more lenses. For example, the optical beam may be collimated by a collimator and expanded by a beam expander. In some instances, the collimator includes a first lens and the beam expander is a refractive telescope containing a second lens and a third lens. In some implementations, the first, second and third lenses using during operation 102 may be configured in parallel and oriented in a direction perpendicular to a propagation direction of the optical beam. In some instances, the optical beam after operation 102 may be transformed to an expanded collimated optical beam on the first portion 110A of the beam path 110.

In some implementations, prior to the broadening of the optical beam, the optical beam may be guided from the attenuator to a single-mode optical fiber. In some implementations, the single-mode optical fiber may be used to improve the quality of the optical beam. In some implementations, the single-mode optical fiber is used to polish the beam, including the phase and/or intensity profiles of the optical beam. For example, a single-mode optical fiber filters out higher-order modes as well as any beam distortions to obtain a nearly Gaussian profile from the fiber. In some instances, a single-mode optical fiber is used as a spatial filter. In some instances, a polarization-maintaining single-mode optical fiber may be used to maintain the polarization state of the optical beam. In some implementations, a multi-mode fiber may be used to maintain the intensity of the optical beam without significant attenuation.

At 104, a structured optical beam is prepared. In some implementations, a structured optical beam having position-dependent polarizations, e.g., polarization directions that vary at different positions in the cross-section of the structured optical beam, may be obtained on a second portion 110B of the beam path 110. The general form of the traverse wavefunction of a spatially dependent optical state travelling along the z-direction is given by:

$$|\Psi\rangle = \alpha(r,\varphi)|R\rangle + \beta(r,\varphi)|L\rangle$$

where $\alpha(r, \varphi)$ and $\beta(r, \varphi)$ are complex functions, and $|R\rangle$, $|L\rangle$ denote right and left circular polarizations, respectively. In some implementations, the structured optical beam on the second portion 110B prepared during operation 104 may be an optical beam with spatially dependent Pancharatnam-Berry geometrical phases. In some implementations, the structured optical beam may be, for example, "vector vortex beams", "spin-orbit beams", orbital angular momentum (OAM) beams, Bessel beams or Airy beams, in which spin is coupled to different spatially dependent phase profiles.

In some implementations, the structured optical beam may be obtained by passing the optical beam through optical components that impart a spatially dependent structure on the optical beam. For instance, the structured optical beam may be obtained by passing the expanded collimated optical beam on the first portion 110A through polarization components in combination with one or more of the following types of components: triangular slits, Q-plates, lattice of optical vortices (LOV) prisms, spatial light modulator (SLM), spiral phase plates (SPP), or other optical components, which may be used to induce spatially dependent phase shifts. In some implementations, the structured optical beam may be obtained by passing the expanded collimated beam through an interferometer. In some examples, the interferometer can be implemented as a Michelson interferometer, a Mach-Zehnder interferometer, or another type of interferometer.

In some implementations, a Mach-Zehnder interferometer may include two beam splitters (BS), a transmissive spiral phase plate (SPP), two mirrors and a half wave plate (HWP). In some implementations, prior to passing the prepared beam to the Mach-Zehnder interferometer, a linear polarizer and a quarter wave plate (QWP) are placed in front of a first BS of the Mach-Zehnder interferometer. In some examples, an incident optical beam may become left-circularly polarized after passing through the linear polarizer and the QWP.

In some implementations of a Mach-Zehnder interferometer, an incident optical beam is split by the first BS into two paths and each of the two paths is reflected by a mirror. In some implementations, one of the two paths may be directed through the SPP and the other one of the two paths may be directed through the HWP. In some implementations, the SPP on one path of the Mach-Zehnder interferometer may be used to induce the OAM to the incident optical beam. In some implementations, when an incoming beam with a Gaussian profile is diffracted by the SPP, the optical beam passing through it undergoes a phase-change which induces a "spiral" element to its phase front with a non-zero angular momentum. In some implementations, geometry of the SPP may be selected to induce a desired OAM. In some implementations, the HWP on the other path of the Mach-Zehnder interferometer may be used to prepare the right-circular polarization. In some instances, the split optical beams on the two paths are recombined on a second BS of the Mach-Zehnder interferometer and output as the structured optical beam on the second portion 110B of the beam path 110.

In some implementations, a Michelson interferometer may include a beam splitter (BS), a spatial light modulator (SLM), a mirror, a linear polarizer and one or more quarter wave plates (QWP). In some examples, the BS of the Michelson interferometer, which is partially reflective, may be used to split the incident beam into two paths and create a coherent superposition of the two paths. In some instances, the SLM may be placed in one path (e.g., reflected path) of the Michelson interferometer along with standard polarization components. In some instances, the mirror may be configured in the other path (e.g., transmitted path) of the Michelson interferometer. In some instances, the mirror may be linearly translated on a motorized translation mechanism to control the relative uniform phase shift between the two paths. SLM can be programmed to induce arbitrary spatially dependent phase shifts across the beam profile. Reflected light from the SLM and the mirror may be recombined at the BS and output as the structured optical beam on the second portion 110B of the beam path 110. In some implementations, a QWP is placed in front of the mirror in order to induce a polarization flip and another QWP may be placed at the output of the Michelson interferometer.

In some implementations, the structured optical beam, obtained by passing the optical beam through one or more polarization components and the interferometer, is a coherent superposition of right circularly polarized light with no OAM and left circularly polarized light with a non-zero OAM of $\ell$. The form of the traverse wavefunction of the structured optical beam travelling along the z-direction is given by:

$$|\psi_{out}\rangle = \frac{1}{\sqrt{2}}\left(|R\rangle + e^{i\ell\varphi}|L\rangle\right) = \frac{1}{\sqrt{2}}\left(|0, R\rangle + |\ell, L\rangle\right)$$

where $\ell$ is the OAM number of the left circularly polarized light and $\varphi$ is the azimuthal coordinate.

At 106, the structured optical beam is focused. In some implementations, a focused, structured optical beam may be obtained on a third portion 110C of the beam path 110. In some implementations, the structured optical beam may be focused onto a region where a human eye (e.g., onto the retina of a human eye) can directly observe the structured optical beam. In some implementations, the focused, structured optical beam may be obtained by using one or more lenses. In some implementations, a speckle pattern may be observed when the eye is exposed to monochromatic coherent light. In some instances, such a speckle pattern may be removed from the light beam to avoid interfering with the observer's ability to clearly perceive the position-dependent polarizations in the structured optical beam. In some implementations, a speckle pattern may be removed by overlaying multiple structured beams (with the same spatially dependent polarization profiles) which produce distinct speckle patterns. In some implementations, multiple monochromatic laser sources with distinct wavelengths may be used to create the distinct speckle patterns. For example, multiple laser sources with wavelengths in a range of 450-470 nanometers (nm) which may appear identical in colour, can produce distinct speckle patterns. In some implementations, a diffusing element may be placed in the optical path 110 to remove the speckle pattern. In some implementations, the scattering of angle and distance from the diffusing element to the observer may be configured such that a displacement of the optical rays caused by the diffusing element is comparable to the size of each speckle in the speckle pattern.

In some implementations, a speckle pattern may be removed by vibrating the one or more optical elements along the beam path 110. In some implementations, each of the one or more optical elements that may be vibrated for removing the speckle patterns may include a non-planar surface. For example, the one or more lenses for collimating and broadening the optical beam, and the SPP in the interferometer to induce the OAM to the incident optical beam may be vibrated perpendicular to the propagation direction of the optical beam. In some implementations, the amplitude of the vibration may be greater than the size of each speckle in the speckle pattern, and the frequency of the vibration is greater than an observer's capability to perceive (e.g., >60 Hz).

In some implementations, a vibrating lens may be configured at the end of the beam path 110 before reaching the observation region. In some implementations, the vibrating lens may have a large focal length to make it easier for the human eye to focus. In some implementations, a vibrating lens with a large focal length may avoid strong focusing effects which may significantly alter the position-dependent polarizations in the optical beam. In some implementations, the focal length of the vibrating lens for removing a speckle pattern may be optimized for highest subjective contrast. For example, the focal length may be in the range of 10 cm to 30 cm.

Figure 2:
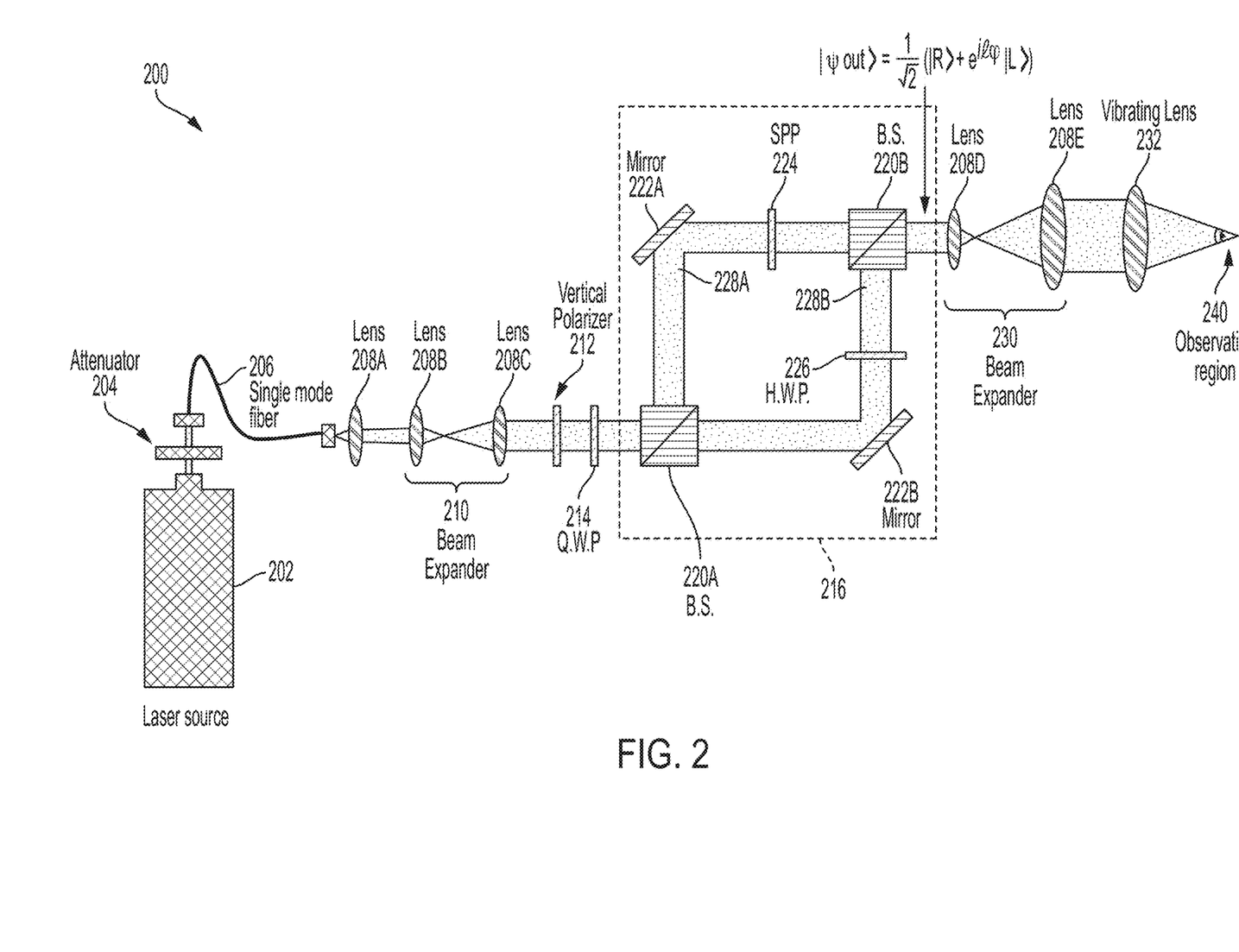
FIG. 2 is a schematic diagram showing an example optical system.
Figure 3:
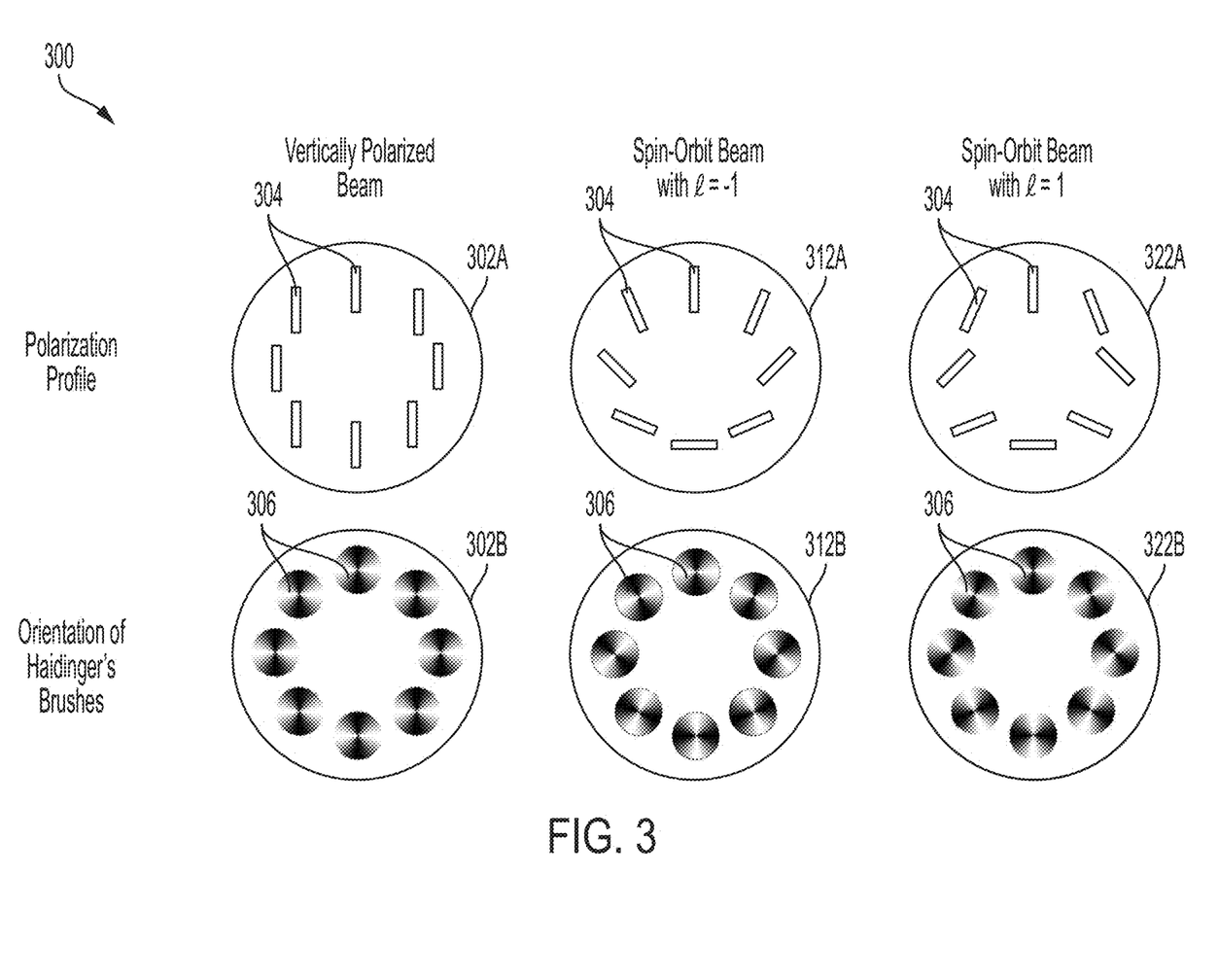
FIG. 3 is a plot showing examples of position-dependent polarization profiles in structured optical beams and corresponding position-dependent profiles of Haidinger's brushes observed in a human eye.

In some implementations, the example process 100 to obtain a structured optical beam shown in FIG. 1 may be performed by the example optical system 200 shown in FIG. 2, and examples of position-dependent polarization profiles of a structured optical beam and corresponding Haidinger's brushes induced in the human eye are shown in FIG. 3. In some implementations, the example process 100 may be implemented in another manner (e.g., using different components or a different arrangement of the same components), and may generate other types of structured optical beams (e.g., having different position-dependent polarization profiles that produce other types of Haidinger's brushes).

FIG. 2 is a schematic diagram showing an example optical system 200 that is used to perform the example process 100 shown in FIG. 1. In some instances, the optical system 200 shown in FIG. 2 may be used for human detection of OAM numbers, quantifying spin-orbit beams, or another purpose.

In the example shown in FIG. 2, the optical system 200 includes a series of optical elements that define one or more beam paths between a laser source 202 and an observation region 240. In the example shown, the series of optical elements in the example optical system 200 includes an attenuator 204, a single mode fiber 206, a lens 208A, a first beam expander 210, a linear polarizer 212, a quarter wave plate (QWP) 214, an interferometer 216, a second beam expander 230 (which includes a pair of lenses 208D, 208E in the example shown), and a vibrating lens 232. In the example shown, the first beam expander 210 includes a pair of lenses 208B, 208C, and the interferometer 216 is implemented as a Mach-Zehnder interferometer. In some examples, the optical system 200 may include additional or different components, and the components may be arranged as shown or in another manner.

In the example shown in FIG. 2, the laser source 202 generates a laser beam. In the example shown, the laser beam comprises coherent monochromatic light. In some implementations, the laser source 202 produces a blue laser with a mean wavelength in a range of 450-470 nm. For example, because the human perception of the Haidinger's brushes has been found to be optimal for a wavelength at about 460 nm, the laser source 202 may be have a mean wavelength of 460 nm. Light having another wavelength profile or distribution may be used in some cases.

In some implementations, the attenuator 204 is positioned to receive an output light beam from the laser source 202. In some implementations, the attenuator 204 may be configured to ensure that the exposure irradiance level of the laser beam is below the Maximal Permissible Exposure (MPE) for human perception. For instance, the attenuator 204 may provide an output light beam that conforms to the guidelines for laser exposure time outlined by the International Commission on Non-Ionizing Radiation. For example, the MPE value for sustained exposure to light with wavelength about 460 nm is $10^{-4}$ W m$^{-2}$. Accordingly, the attenuator 204 may be configured to attenuate the light beam to an exposure irradiance level below $10^{-4}$ W m$^{-2}$ or another level that is safe for direct viewing by the human eye. In some examples, the attenuator 204 may be a neutral-density filter.

In the example shown, the single-mode optical fiber 206 guides the laser beam from the attenuator 204 to the lens 208A. In some implementations, the single-mode optical fiber 206 is used to improve the quality of the laser beam. For instance, the single-mode optical fiber 206 can be used to polish the phase and/or the intensity profiles of the laser beam. In some instances, the single-mode optical fiber 206 is used as a spatial filter. In some instances, the single-mode optical fiber 206 strips off light in the higher-order modes as well as any beam distortions to obtain a nearly Gaussian profile at its output.

In some implementations, the laser beam is then collimated by the lens 208A and further expanded by the beam expander 210. In some implementations, the laser beam is expanded to a size that covers 3 to 5 degrees (or another range of angles) of the field of view of the human eye. In some instances, the beam expander 210 is a refractive telescope including a pair of lenses 208B, 208C. In some implementations, the lens 208A and the pair of lenses 208B, 208C in the beam expander are configured in parallel and oriented in a direction perpendicular to the incident direction of the laser beam.

In some implementations, the expanded, collimated laser beam exiting the first beam expander 210 is then guided through the interferometer 216. In the example optical system 200 as shown in FIG. 2, the interferometer 216 is implemented as a Mach-Zehnder interferometer. The example Mach-Zehnder interferometer 216 includes two beam splitters (BS) 220A, 220B, a first mirror 222A followed by a spiral phase plate (SPP) 224 along a first beam path 228A between the beam splitters 220A, 220B, and a second mirror 222B followed by a half-wave plate (HWP) 226 along a second beam path 228B between the beam splitters 220A, 220B. A Mach-Zenhnder interferometer may be implemented in another manner (e.g., with additional or different features) in some cases.

In some implementations, prior to passing the expanded, collimated laser beam from the first beam expander 210 to the Mach-Zehnder interferometer 216, a linear polarizer 212 and a quarter wave plate (QWP) 214 may be placed in front of the first BS 220A of the Mach-Zehnder interferometer 216. In some instances, a linear polarizer 212 may be a polarizing filter which allows light waves of a specific polarization direction to pass through. For example, the linear polarizer 212 allows only vertically polarized light waves to pass through. In some instances, a quarter wave plate 214 may retard the component along one direction ("slow" axis) relative to the perpendicular direction ("fast axis") and prepare circularly polarized light. In this case, the optics axis of the QWP may be oriented 45 degrees relative to the polarization of the incoming light. In some examples, the expanded, collimated laser beam after passing through the linear polarizer 212 and the QWP 214 may become left-circularly polarized.

In some implementations, the left-circularly polarized, collimated beam is then split by the first BS 220A into two beam paths and each of the two beam paths are reflected by the mirrors 222A, 222B. Before being recombined on the second BS 220B, the first beam path 228A may be directed through the SPP 224, which induces the azimuthally varying phase shift, and the second beam path 228B may be directed through the HWP 226, which changes the polarization state to right-circular polarization. In some implementations, the SPP 224 may be configured with a winding "staircase" structure, which introduces a spiral phase shift to and increase the angular momentum of the left-circularly polarized light beam when passing through the SPP 224. In some implementations, the HWP 226 may be used to shift the polarization direction which flips the left-circularly polarized light beam to a right-circularly polarized light beam.

In some implementations, a structured optical beam may be obtained by combining the two beam paths 228A, 228B on the second BS 220B. In the example shown, the intensity of the structured optical beam may be uniform across the cross-section of the structured optical beam. In the example optical system 200 as shown in FIG. 2, the structured optical beam at the output of the interferometer 216 may be a coherent superposition of right-circularly polarized light with no OAM and left circularly polarized light with an OAM of $\ell$. The form of the traverse wavefunction of the structured optical beam travelling along the z-direction is given by:

$$|\psi_{out}\rangle = \frac{1}{\sqrt{2}}\left(|R\rangle + e^{i\ell\varphi}|L\rangle\right) = \frac{1}{\sqrt{2}}\left(|0, R\rangle + |\ell, L\rangle\right)$$

where $\ell$ is the OAM number of the left circularly polarized light, $\ell \neq 0$, and $\varphi$ is the azimuthal coordinate.

In some implementations, the structured optical beam may be further expanded by the second beam expander 230 and focused by the vibrating lens 232 to an observation region 240. In some instances, a speckle pattern caused by the monochromatic coherent light may be removed by the vibrating lens 232. In some implementations, the amplitude of the vibration may be greater than the size of each 'speckle' in the system, and the frequency of the vibration may be greater than the observer's capability to perceive (e.g., >60 Hz).

In some implementations, the vibrating lens 232 may have a large focal length to make it easier for a human eye in the observation region 240 to focus on. In some implementations, the vibrating lens 232 with a large focal length may avoid strong focusing effects which may significantly alter the position dependent polarizations in the structured optical beam. In some implementations, the focal length of the vibrating lens 232 for removing a speckle pattern may be optimized for highest subjective contrast. For example, the focal length may be in the range of 10 cm to 30 cm.

In some implementations, when the structured optical beam with position-dependent polarizations in the cross-section of the beam is incident on a human eye in the observation region 240, and the human eye looks at a position away from the center of the structured optical beam, the orientation direction of the Haidinger's brush observed at that position depends on the local polarization direction in the structured optical beam. In some cases, the orientation direction of the Haidinger's brush is measured as the orientation direction of the double-ended brush in the Haidinger's brush.

In some implementations, when the structured optical beam with position-dependent polarizations in the cross-section of the beam is incident on a human eye in the observation region 240, and the human eye looks at the center of the structured optical beam where there is a large spatial polarization gradient, azimuthal fringes may be observed by the human eye. Unique entoptic profiles are induced by the interaction between the polarization gradients in an optical beam and the radially symmetric dichroic elements that are centered on the foveola in the macula of the human eye. In some instances, the azimuthal fringes, which correspond to the position-dependent polarization profile of the structured optical beam, may be made to rotate by inducing a phase shift on the polarization degree of freedom. In some examples, the number of azimuthal fringes when viewing a polarization coupled OAM beam may be equal to $|(\ell_1-\ell_2)-2|$, where $\ell_1$ is the OAM coupled with the right circular polarization and $\ell_2$ is coupled to the left circular polarization.

In some implementations, the position-dependent profiles of Haidinger's brushes observed by the human eye in the observation region 240 may be used as feedback from the observer. In some implementations, such feedback may be collected using an input device of a computer system (e.g., a mouse, touchpad, button, keypad, or otherwise) or another type of feedback mechanism. In some implementations, the feedback from the observer may include a report on observed features, e.g., the spatially dependent orientation of Haidinger's brushes while the observer looks at different parts of the beam where the eye's field of view is illuminated by a structured optical beam with uniform polarization. In some cases, the feedback from the observer may include a report on the observed features, e.g., a specific pattern while the observer looks at a specific part of a structured optical beam where the eye's field of view is illuminated by the structured optical beam with a polarization gradient (e.g., position-dependent polarization directions). In some cases, the observed features in the feedback may include spatially dependent specific patterns while the observer looks at different parts of a structured optical beam where the eye's field of view is illuminated by the structured optical beam with a position dependent polarization directions (e.g., polarization gradients). In some examples, the feedback from the observer may include information of the observed features, such as the clarity and structure. In some implementations, the feedback from the observer may be provided to an algorithm which may be analyzed by the computer system, or to a medical professional to determine structure and the functionality of the macula.

FIG. 3 is a plot 300 showing examples of position-dependent polarization profiles in a cross-section of a structured optical beam and corresponding profiles of Haidinger's brushes, as they may be observed by a human eye. As shown in FIG. 3, each of the position-dependent polarization profiles 302A, 312A, 322A shows a cross-sectional view of a structured optical beam and each of the position-dependent polarization profiles 302A, 304A, 306A contains multiple position-dependent polarizations 304 in the cross-section of the structured optical beam. This polarization profile corresponds to $$|\psi\rangle = \frac{1}{\sqrt{2}}(|R\rangle + e^{i\ell\varphi}|L\rangle),$$

where $\ell = +1, -1$ for the two cases. In some instances, the position-dependent polarizations 304 are located at positions away from the center of the structured optical beam. In some instances, the intensity is uniform across the structured optical beam.

In some implementations, when the structured optical beam with position-dependent polarizations 304 is incident on a human eye and when the eye is focused on positions in the structured optical beam where the position-dependent polarizations are located, Haidinger's brushes 306 may be observed at the respective positions. In some instances, the orientation of the Haidinger's brushes 306 may be determined by the directions of the corresponding position-dependent polarization 304. In some examples, the orientation direction of the Haidinger's brush 306 is measured as the orientation direction of the double-ended brush (e.g., black bow tie).

In some implementations, the structured optical beam may be produced using an optical system (e.g., the optical system 200 as shown in FIG. 2) and focused on a human eye (e.g., positioned in the observation region 240). In this case, when the human eye looks at a position with a local uniform polarization, the human eye may perceive a Haidinger's brush 306 with an orientation direction aligned with in the direction of the local polarization 304 at that position.

In the example shown in FIG. 3, each of the position-dependent polarization profiles 302A, 312A, 322A may include regions of roughly uniform position-dependent polarizations 304. For example, eight position-dependent polarizations 304 in a first polarization profile 302A are oriented along the same vertical direction. For example, position-dependent polarizations 304 are oriented in different directions at different regions (e.g., vertically polarized in the top region and horizontally polarized in the bottom region) in the second polarization profile 312A and the third polarization profile 322A. In some implementations, the second position-dependent polarization profile 312A may be produced by a structured optical beam with at an orbital angular momentum (OAM) of 1 (e.g., a spin-orbit beam with $\ell = 1$) and the third position-dependent polarization profile 322A may be produced by a different structured optical beam with at an orbital angular momentum (OAM) of −1 (e.g., a spin-orbit beam with $\ell = -1$).

In some cases, regions with circularly polarized light may be present, and as a circularly polarized light is not axis dependent, the orientation directions of the Haidinger's brushes is independent of the rotation of the head of the observer. Hence looking the optical beam and rotating the observer's head allows a person to determine the polarization state of light.

In some implementations, the feedback from the human observing the structured light beam can be used for diagnosis or analysis of the human's eye. For example, the feedback may be useful for diagnosis of central visual field dysfunctions and age-related macular degeneration (AMD). For example, the ability to clearly see and correctly differentiate between various structured optical beams may indicate that the macula of the observer is healthy and properly structured. In some implementations, structure and the functionality of the macula may be determined by providing the feedback about the clarity and structure of the observed features to a computer system or a medical professional for evaluation.

In a general aspect of what is described above, a structured optical beam with position-dependent polarizations is prepared for human observation.

In a first example, an optics method includes processing an optical beam to produce a structured optical beam for human observation. Processing the optical beam includes receiving the optical beam from a laser source; attenuating the optical beam to an exposure irradiance level that is safe for direct viewing by a human eye; expanding the optical beam to a size configured for a field of view of the human eye; and preparing the optical beam with a position-dependent polarization profile; and directing the structured optical beam towards an observation region for human observation. The structured optical beam includes the position-dependent polarization profile.

Implementations of the first example may include one or more of the following features. Receiving the optical beam from the laser source includes receiving a blue optical beam with a mean wavelength between 450 and 470 nanometers. Attenuating the optical beam includes attenuating the optical beam to the exposure irradiance level less than $10^{-4}$ W m$^{-2}$. Expanding the optical beam includes expanding the optical beam to a size configured to cover a range that is larger than 3 degrees of the field of view of the human eye. Processing the optical beam includes removing speckle patterns in the structured optical beam. Removing the speckle patterns includes at least one of: passing the optical beam through an optical element with a vibrating motion a direction perpendicular to the propagation direction of the optical beam; receiving the optical beam from a laser source having a broad wavelength distribution; or introducing the optical beam to a diffusing element.

Implementations of the first example may include one or more of the following features. Directing the structured optical beam includes passing the structured optical beam through lenses to focus the structured optical beam onto the retina of the human eye. Expanding the optical beam includes passing the optical beam through one or more lenses. Processing the optical beam includes transmitting the optical beam through a single mode fiber from the attenuator to a collimating lens. Processing the optical beam includes: after attenuating the optical beam, expanding the optical beam to the size configured for the field of view of the human eye; and after preparing the optical beam with the position-dependent polarization profile, removing speckle patterns in the optical beam. Preparing the optical beam with a position-dependent polarization profile includes passing the optical beam through an interferometer. The optics method further includes after directing the structured optical beam, receiving feedback from a (human) subject; and providing the feedback from the subject for analysis of the human eye of the subject.

In a second example, a system includes a laser source configured to produce an optical beam; an optical system that processes the optical beam to produce a structured optical beam for human observation. The optical system includes: an attenuator configured to attenuate the optical beam to an exposure irradiance level that is safe for direct viewing by a human eye; a first optical element configured to expand the optical beam to a size configured for a field of view of the human eye; a second optical element configured to prepare the optical beam with a position-dependent polarization profile; a third optical element configured to direct the structured optical beam towards an observation region for human observation. The structured optical beam includes the position-dependent polarization profile.

Implementations of the second example may include one or more of the following features. The laser source is configured to produce a blue optical beam with a mean wavelength between 450 and 470 nanometers. The attenuator is configured to attenuate the optical beam to the exposure irradiance level less than $10^{-4}$ W m$^{-2}$. The first optical element includes one or more lenses configured to expand the optical beam to the size configured to cover a range that is larger than 3 degrees of the field of view of the human eye. The system further includes a fourth optical element configured to remove speckle patterns in the structured optical beam, wherein the fourth optical element comprises a vibrating lens. The third optical element includes one or more lenses configured to focus the structured optical beam onto the retina of the human eye.

Implementations of the second example may include one or more of the following features. The optical system includes a collimation lens that collimates the optical beam; and a single mode fiber configured to direct the optical beam from the laser source to the collimation lens. The optical system defines an optical path for the optical beam from the laser source to the observation region. The optical system includes: the single mode fiber after the attenuator along the optical path; the collimation lens after the single mode fiber along the optical path; a beam expander after the collimation lens along the optical path; a linear polarizer after the beam expander along the optical path; a quarter wave plate after linear polarizer along the optical path; an interferometer after the quarter wave plate along the optical path; and one or more lenses after the interferometer along the optical path. The second optical element includes an interferometer. The second optical element further includes a linear polarizer and a quarter wave plate.

While this specification contains many details, these should not be understood as limitations on the scope of what may be claimed, but rather as descriptions of features specific to particular examples. Certain features that are described in this specification or shown in the drawings in the context of separate implementations can also be combined. Conversely, various features that are described or shown in the context of a single implementation can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single product or packaged into multiple products.

A number of examples have been described. Nevertheless, it will be understood that various modifications can be made. Accordingly, other examples are within the scope of the following claims.

What is claimed is:

1. An optics method comprising:
   processing an optical beam to produce a structured optical beam for human perception of optical polarization, wherein processing the optical beam comprises:
      receiving the optical beam from a laser source;
      attenuating the optical beam to an exposure irradiance level that is safe for direct viewing by a human eye of a subject;
      expanding the optical beam to a size configured for a field of view of the human eye; and
      preparing the optical beam with a position-dependent polarization profile;
   illuminating the field of view of the human eye with the structured optical beam by directing the structured optical beam towards the human eye, wherein the structured optical beam comprises the position-dependent polarization profile, and illuminating the field of view of the human eye with the structured optical beam induces an entoptic profile that allows the human subject to perceive the position-dependent polarization profile.

2. The method of claim 1, wherein receiving the optical beam from the laser source comprises receiving a blue optical beam with a mean wavelength between 450 and 470 nanometers.

3. The method of claim 2, wherein attenuating the optical beam comprises attenuating the optical beam to the exposure irradiance level less than $10^{-4}$ W m$^{-2}$.

4. The method of claim 1, wherein expanding the optical beam comprises expanding the optical beam to a size configured to cover at least 3 degrees of the field of view of the human eye.

5. The method of claim 1, wherein processing the optical beam comprises removing speckle patterns in the structured optical beam.

6. The method of claim 5, wherein removing the speckle patterns comprises at least one of:
   passing the optical beam through an optical element with a vibrating motion in a direction perpendicular to a propagation direction of the optical beam;
   receiving the optical beam from a laser source having a broad wavelength distribution; or
   introducing the optical beam to a diffusing element.

7. The method of claim 1, wherein directing the structured optical beam comprises passing the structured optical beam through lenses to focus the structured optical beam onto the retina of the human eye.

8. The method of claim 1, wherein expanding the optical beam comprises passing the optical beam through one or more lenses.

9. The method of claim 1, wherein processing the optical beam comprises transmitting the optical beam through a single mode fiber from the attenuator to a collimating lens.

10. The method of claim 1, wherein processing the optical beam comprises:
    after attenuating the optical beam, expanding the optical beam to the size configured for the field of view of the human eye; and
    after preparing the optical beam with the position-dependent polarization profile, removing speckle patterns in the structured optical beam.

11. The method of claim 1, wherein preparing the optical beam with the position-dependent polarization profile comprises passing the optical beam through an interferometer.

12. The method of claim 1, further comprising:
    after directing the structured optical beam, receiving feedback from the subject in response to the induced entoptic profile; and
    providing the feedback from the subject for analysis of the human eye of the subject.

* * * * *